Figure 1:
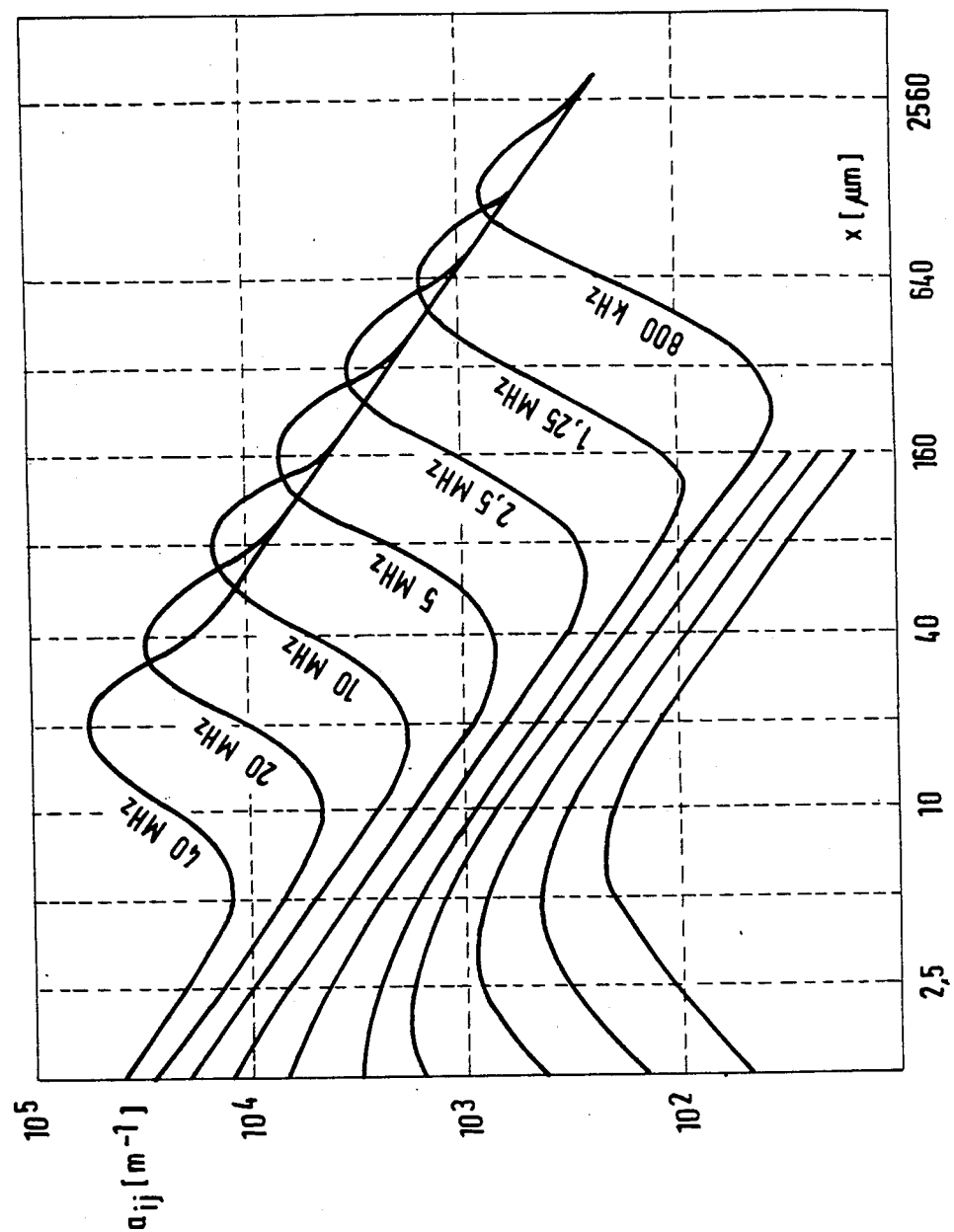

United States Patent [19]

Riebel

[11] Patent Number: 4,706,509
[45] Date of Patent: Nov. 17, 1987

[54] METHOD OF AND AN APPARATUS FOR ULTRASONIC MEASURING OF THE SOLIDS CONCENTRATION AND PARTICLE SIZE DISTRIBUTION IN A SUSPENSION

[75] Inventor: Ulrich Riebel, Kronberg, Fed. Rep. of Germany

[73] Assignee: Friedrich Loffler, Karlsruhe, Fed. Rep. of Germany

[21] Appl. No.: 887,158
[22] PCT Filed: Oct. 23, 1985
[86] PCT No.: PCT/EP85/00560
§ 371 Date: Jun. 16, 1986
§ 102(e) Date: Jun. 16, 1986
[87] PCT Pub. No.: WO86/02727
PCT Pub. Date: May 9, 1986

[30] Foreign Application Priority Data

Oct. 23, 1984 [DE] Fed. Rep. of Germany ....... 3438798

[51] Int. Cl.[4] ..................... G01N 15/02; G01N 15/06; G01N 29/02
[52] U.S. Cl. ...................... 73/865.5; 73/28; 73/61 R
[58] Field of Search ...................... 73/865.5, 61 R, 38, 73/28

[56] References Cited

U.S. PATENT DOCUMENTS 3,779,070 12/1973 Cushman et al. .................. 73/865.5
3,802,271 4/1974 Bartelson ........................... 73/865.5

FOREIGN PATENT DOCUMENTS 182549 10/1983 Japan .
1410954 10/1975 United Kingdom .

OTHER PUBLICATIONS

R. J. Urich, "The Absorption of Sound in Suspensions of Irregular Particles," *The Journal of the Acoustical Society of America*, vol. 20, No. 3, (May 1948), pp. 283-289.

Primary Examiner—Michael J. Tokar
Assistant Examiner—Joseph W. Roskos
Attorney, Agent, or Firm—Pennie & Edmonds

[57] ABSTRACT

Simultaneous measuring of the concentration of solids and particle size distribution in a suspension is effected by exciting the suspension by ultrasonic waves of a plurality of frequencies, the wavelength at the lowest frequency being greater than the diameter of the largest particles to be expected and the wavelength of the highest frequency being smaller than the diameter of the smallest particles to be expected. The dimensional spectrum of the solid particles is divided into a plurality of dimensional intervals for which the respective solids concentrations are determined by measuring the radiation absorption of each frequency used for irradiation and representing the same as the sum of the products of the absorption coefficients which are specific of the frequency and dimensional interval with the unknown particle concentrations. This results in a linear system of equations which is solved with respect to the unknown concentrations.

14 Claims, 2 Drawing Figures

METHOD OF AND AN APPARATUS FOR ULTRASONIC MEASURING OF THE SOLIDS CONCENTRATION AND PARTICLE SIZE DISTRIBUTION IN A SUSPENSION

The invention relates to a method of simultaneously measuring the concentration of solids and the particle size distribution in a suspension, wherein the suspension is excited by ultrasonic waves of more than one frequency and the absorption thereof by the solid particles is measured and evaluated. The invention also relates to an apparatus for carrying out such a method.

Suspensions are encountered frequently in the recovery and processing of raw materials, in the chemical industry, and in the preparation of foodstuffs. A suspension in the instant case is to be understood not only as a fine distribution of very small particles of a solid substance in a liquid but, quite generally, also as the distribution of minute droplets of an insoluble liquid or of gas bubbles in a fluid. The monitoring and control of such processes of industrial processing engineering often requires measurements to be taken of the concentration and dimensional distribution of the particles. As the measurement and control usually are being made with a flowing system, the following requirements must be met:

(a) The measurement is to be made instantaneously, in other words, the result of the measurement is to be available after a period of time during which the flowing suspension has not covered any substantial distance;

(b) the flowing system is not to be influenced by the measurement; rement;

(c) sampling is to be avoided, especially if the substance concerned is poisonous, caustic, hot, or highly pressurized.

As a result of these conditions the particle concentration and particle size distribution cannot be determined by screen or sedimentation analyses (sedimentation scale or photosedimentation meter). Other methods, like the measurement of the scattering of a laser beam, although meeting the above requirements, are restricted to transparent media. Also the method of the so-called Coulter counter is limited to certain electrically conductive fluids and, moreover, very susceptible to disturbances as the narrow capillary needed for measurement is plugged up easily.

Methods employing ultrasonic waves, on the other hand, are applicable with any fluid which can be excited by the same. As is well known, the reduction in intensity of radiation in an absorbing medium is defined by Beer's law into which enters the coefficient of absorption. A method of measuring the solids concentration in a suspension by means of ultrasound is known from DE-OS No. 22 57 802. In that case the suspension is excited by ultrasonic waves of two frequencies, and the dampening of the radiation intensity by absorption is measured. The absorption data among others are used for calculating the percentage volume share of solid particles and the mean geometric particle diameter. If the laws of statistics according to which the particles are formed were known, these data might be used for an exact determination of the particle size distribution. However, as a rule, this is not the case, in other words, the particle size distribution does not follow a known function. For this reason the method known from DE-OS No. 22 57 802, although permitting indications of individual parameters of the particle size distribution, does not permit a definition of the particle size distribution itself. The two frequencies of the ultrasonic waves in that case are selected such that the absorption is sensitively dependent on the characteristic parameters of the suspension. As a result, the frequencies are selected rather closely together.

It is the object of the invention to provide a method of and an apparatus for measuring the concentration of solids and the particle size distribution in a suspension which will meet the above mentioned requirements (a) to (c) and permit an accurate measurement of the particle size distribution. bution.

A method solving this problem and a corresponding apparatus are characterized in the claims.

With any given suspension, normally, the limits within which the diameters of the particles lie are well known. For this reason it is possible to fix two frequencies for a given suspension such that the wavelength belonging to the higher frequency is smaller than the diameter of the smallest particle to be expected and the wavelength of the lower frequency is greater than the diameter of the largest particles to be expected. This is possible even if the particle sizes are not known at all because the frequencies available between 100 kHz and approximately 100 MHz permit coverage of the entire range of particle sizes which usually occur. Moreover, the coefficients of absorption of the solid particles at a given frequency of the ultrasonic wave in response to the particle size are known.

By good approximation the coefficient of absorption for a given frequency may be considered to be constant in a particle size interval $\Delta x_i$ of limited length.

In accordance with the invention the particle size distribution, in other words, the concentration of particles as a function of their size is determined in the form of a step function. The increment of the step function are the particle size intervals which may be given any desired small value, in response to the desired accuracy. For example, ten particle size intervals should be sufficient to determine a sufficiently accurate particle size distribution. The particle size distribution in that case results from the determination of the corresponding concentration of solid particles of this dimension with respect to each particle size interval. In other words, the concentrations of particles of a series of particle size intervals must be determined respectively in order to determine a particle size distribution.

The unknown concentrations of the solid particles of a particle size interval each are determined, in accordance with the invention, in that the suspension is excited by a plurality of ultrasonic waves of different respective frequencies $f_j$ and that the absorption of the wave is measured for each frequency. As particles of each dimensional interval take part in the absorption in correspondence with the coefficient of absorption to be regarded as being known for this frequency and the dimensional interval, the overall absorption measured $A_j$ is to be represented as the sum across all particle size intervals, the frequency being a constant parameter.

If the overall dimensional spectrum of the solid particles is divided into n intervals, it will be necessary to determine n unknown concentrations $c_i$ of solid particles for each dimensional interval $\Delta x_i$. Since a single linear equation does not permit the calculation of several unknown quantities, a plurality of frequencies $f_j$ are used for radiation so that the result will be a linear system of equations.

An unambiguous solution of a linear equation system including n unknown quantities requires a total of n linearly independent equations. For this reason it is provided in a special modification of the invention that the number of different frequencies of the ultrasonic waves equals the number of particle size intervals.

Under especially favorable conditions, even a smaller number of frequencies will be sufficient although the equation system in that case will comprise several vectors of solution among which, however, the solution vector looked for can be determined by way of other marginal conditions. In any particle size distribution there is a certain dimensional relationship between the concentrations looked for of the individual particle intervals. Starting from low concentration values in the marginal range of the dimensional intervals, the concentration will rise steadily to medium values and then drop. In a great number of cases, based on this marginal condition, it will be possible to determine the solution looked for of the unknown concentrations even if the number of ultrasonic waves of different frequencies is smaller than the number of particle size intervals.

Under especially unfavorable conditions, on the other hand, it may be attempted to improve the accuracy of the measurement by selecting a greater number of measuring frequencies than the number of particle size intervals.

It is obvious that the overall solids concentration results directly from the solid particle size distribution by integration (summing) of the individual concentration values in the dimensional intervals.

The diameter of the particles which must not always be solid particles, as follows from the above, but also may be gaseous or liquid particles, is understood to be the so-called equivalent diameter which corresponds to the effective cross section of the particles. In this manner a defined diameter may be associated also with particles which are not spherical.

The apparatus according to the invention for measuring the particle size distribution is characterized by a means for generating a plurality of ultrasonic waves of different frequencies. It follows from the above that the frequencies $f_j$ are selected such that the wavelength corresponding to the lowest frequency $f_1$ is greater than the diameter of the largest particles to be expected, while the wavelength to be associated with the highest frequency $f_m$ is smaller than the diameter of the smallest particles to be expected. As regards the relationship of the wavelengths $\lambda_j$ with respect to the particle size diameters x, it should be observed that the frequencies $f_j$ need not necessarily fulfill exactly the above mentioned conditions. Fulfilling this condition, on the other hand, ensures that the contribution of the fraction $x_i$ to the overall absorption $A_j$ is measured for all classes $x_i$ of particle sizes, both in the range $x_i > \lambda_j$ and in the range $x_i < \lambda_j$. As the coefficients of absorption $a_{ij}$ in the range $x = \lambda$ experience a particularly distinct change, this guarantees that the maximum measuring accuracy possible will be achieved. If there is uncertainty as to the particle sizes to be detected, the measuring range of the instruments should be made broad from the very beginning by a corresponding choice of frequencies.

In accordance with a preferred modification of the apparatus according to the invention the required number of different ultrasonic transmitters may be reduced by exploiting fundamentals and harmonics of a transmitter. The fundamentals and harmonics may be excited individually in successive time periods, or they may be excited all at the same time and received and measured as well.

The expenditure caused by structural components may be reduced further if the measurements are made according to the pulse echo procedure. In that event the same piezoelectric oscillator serves intermittently as transmitter of a short ultrasonic pulse and as receiver of the echo resulting from reflection at an opposed reflector. The ultrasonic wave thus passes twice through the measuring section.

If the ultrasonic wave transmitters are exited continuously, standing waves are avoided by arranging the absorption distance at an angle other than 90° with respect to the walls enclosing the suspension.

Advantageous modifications of the invention are specified in the subclaims.

Figure 2:
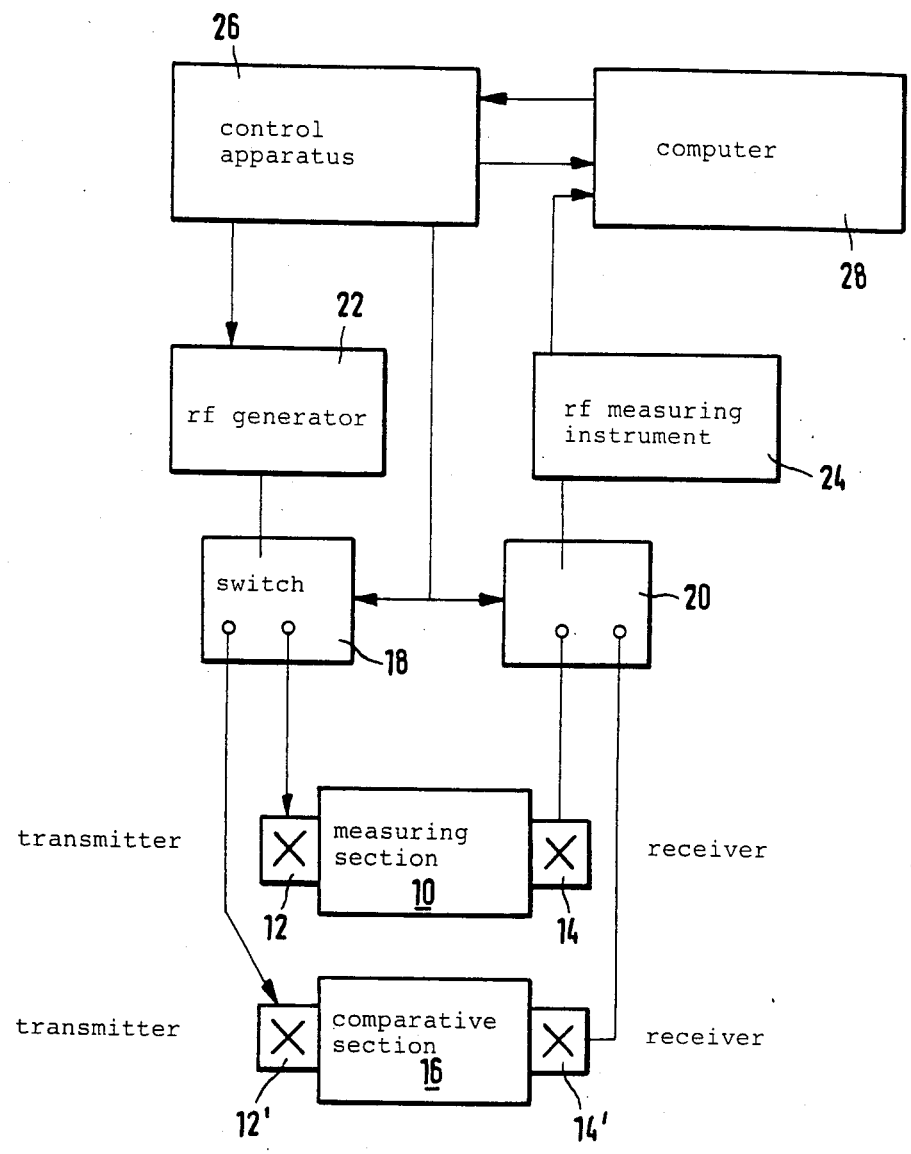

The invention will be described further below with reference to the drawing, in which: FIG. 1 shows the dependence of the coefficient of absorption $a_{ij}$ on the particle size at different frequencies, calculated for suspensions of quartz in water, and FIG. 2 is a diagrammatic presentation of an apparatus for carrying out the method.

A measuring section 10 passes through the flowing suspension of which the solid concentration and particle size distribution are to be determined. The measuring section is defined by an ultrasonic wave transmitter 12 and an ultrasonic wave receiver 14.

Apart from the measuring section 10 passing through the suspension, there is another measuring section 16 crossing the fluid which is free of particles. This additional measuring section serves purposes of zero calibration of the entire measuring apparatus and is furnished with a transmitter 12' and a receiver 14' corresponding to the measuring transmitters and receivers 12 and 14 proper.

Switches 18 and 20 take care that either the measuring section 10 or the comparative measuring section 16 are supplied with excitation frequencies of an rf generator 22 or apply the signal received to an rf measuring instrument 24 for measuring the intensity attenuated by absorption of the ultrasonic waves.

In the drawing, transmitter 12 represents a plurality, i.e. more than just two ultrasonic sources of different frequencies. The manner in which the ultrasonic waves are generated and the suspension is excited by the same as well as the reception and the details of measurement need not be discussed here as those skilled in the art are familiar with the same.

A control apparatus 26 among others serves to preset the frequencies, the intensities, and, if desired, the pulse duration if the pulse echo procedure is used for operation. A computer 28 calculates the particle size distribution and solids concentration in the manner described.

A plurality of m frequencies $f_j$, $1 \leq j \leq m$ are used for excitation such that the wavelength of the ultrasonic waves having the highest frequency $f_m$ approximately corresponds to or is smaller than the diameter $x_{min}$ the smallest particles to be measured and that the wavelength of the ultrasonic waves having the lowest frequency $f_1$ approximately corresponds to or is greater than the diameter $x_{max}$ of the largest particles to be measured.

The absorption measured $A_j$ of the suspension regarding ultrasonic waves of a certain frequency $f_j$ is represented as the following sum:

$$A_j = \sum_{i=1}^{n} a_{ij} c_i$$

wherein $a_{ij}$ = the coefficient of absorption at a certain frequency $f_j$ of those solid particles whose dimension lies in the particle size interval $\Delta x_i$ and $c_i$ = the concentration of the particles of this dimensional interval $\Delta x_i$ in the suspension. The linear equation system thus formed is solved in per se known manner with respect to the unknown quantity $c_i$ as a function of the particle size intervals. And this directly provides the particle size distribution.

What is claimed is:

1. A method of simultaneously measuring the concentration of solid particles and the particle size distribution in a suspension, wherein ultrasonic waves are coupled into said suspension, said ultrasonic waves having more that one frequency and the absorption of said ultrasonic waves by said solid particles is measured, characterized in that (a) a plurality of m frequencies ($f_j$; $1 \leq j \leq m$) of said ultrasonic waves are so selected that the wavelengths of said ultrasonic waves of the highest frequency ($f_m$) approximately corresponds to or is smaller than the diameter $x_{min}$ of the smallest particles to be measured, and that the wavelength of the ultrasonic waves of the smallest frequency ($f_1$) approximately corresponds to or is greater than the diameter $x_{max}$ of the largest particles to be measured;

(b) the absorption ($A_j$) of said ultrasonic waves of said suspension is measured at a given frequency ($f_j$) and expressed by the following equation $$A_j = \sum_{i=1}^{n} a_{ij} c_i \qquad (I)$$

whereby $a_{ij}$ is the absorption-coefficient at said given frequency $f_j$ of those solid particles whose size lies in the particle size interval $\Delta x_i$ and $c_i$ is the concentration of the particles of this dimensional interval $\Delta x_i$ in said suspension, and that (c) the linear equation-system (I) thus formed is solved in per se known manner with respect to the unknown quantities $c_i$ to provide the particle size distribution.

2. The method as claimed in claim 1, characterized in that the number of frequencies equals the number of particle size intervals.

3. The method as claimed in claim 2, characterized in that the number of particle size intervals is selected to be greater than or equal to 5.

4. The method as claimed in claim 3, characterized in that the particle size intervals are formed equidistantly between the logarithms of the diameters of the smallest and largest particles to be expected.

5. The method as claimed in one of the claims 1–3, characterized in that the excitation is effected by an ultrasonic wave band fit for broadband control.

6. The method as claimed in one of claims 1 to 3, characterized in that a plurality of ultrasonic waves of different frequencies are generated by a single oscillator, utilizing harmonics.

7. The method as claimed in any one of the claims 1–4, characterized in that the absorption is measured in pulse-echo operation.

8. The method as claimed in any one of the claims 1–4, characterized in that the suspension is excited by the fundamentals and harmonics of one or more ultrasonic wave transmitters.

9. The method as claimed in claim 8, characterized in that the suspension is excited by one each of the fundamentals and harmonics of one or more transmitters (12) at time intervals in quick succession.

10. The method as claimed in claim 8, characterized in that the absorption of a plurality of frequencies is measured simultaneously, one or more transmitters (12) each being excited simultaneously at the fundamental or one or more of the harmonics.

11. The method as claimed in claim 8, characterized in that in the pulse-echo operation the ultrasonic wave transmitters (12) are used also as receivers, at least one sound reflector being arranged opposite the ultrasonic transmitters (12) in the measuring section.

12. The method as claimed in claim 8, characterized in that the ultrasonic transmitters (12) are excited continuously, and that the absorption section passes at an angle other than 90° through the walls enclosing the suspension.

13. An apparatus for measuring the concentration of solid particles and the particle size distribution in a suspension, comprising means for generating ultrasonic waves of a plurality of frequencies which are so selected that the wavelengths of the ultrasonic waves of the highest frequency ($f_m$) approximately corresponds to or is smaller than the diameter $x_{min}$ of the smallest particles to be measured, and that the wavelengths of the ultrasonic waves of the smallest frequency ($f_1$) approximately corresponds to or is greater than the diameter $x_{max}$ of the largest particles to be measured, means for coupling said ultrasonic waves into said suspension, means for receiving said ultrasonic waves emerging from said suspension and for measuring the absorption $A_j$ of said ultrasonic waves at particular frequencies $f_j$; means for calculating from an equation $$A_j = \sum_{i=1}^{n} a_{ij} c_i \qquad (I)$$

the unknown concentrations $c_i$ of said particles in a dimensional interval $\Delta x_i$, whereby $a_{ij}$ is the coefficient of absorption at one of said particular frequencies $f_j$.

14. The apparatus as claimed in claim 13 characterized in that a plurality of ultrasonic wave transmitters (12) and receivers (14) are provided.

* * * * *